United States Patent [19]

Loken et al.

[11] 4,036,831

[45] July 19, 1977

[54] TRIMETHYL SILOXANE STEROID INTERMEDIATES

[75] Inventors: Bjarte Loken, Rho (Milan); Peter Lindsay MacDonald; Ettore Bigatti, both of Milan, all of Italy

[73] Assignee: Steroid Development Company Establishment, Lugano, Switzerland

[21] Appl. No.: 626,059

[22] Filed: Oct. 28, 1975

[51] Int. Cl.² ............................................. C07J 71/00
[52] U.S. Cl. ........................ 260/239.55 D; 260/397.45
[58] Field of Search .................. 260/239.55 D, 397.45

[56] References Cited

U.S. PATENT DOCUMENTS

| 2,798,118 | 4/1957 | Bernstein et al. | 260/397.45 |
| 2,841,600 | 7/1958 | Hogg et al. | 260/397.45 |

FOREIGN PATENT DOCUMENTS

| 996,080 | 6/1965 | United Kingdom | 260/397.45 |
| 1,227,992 | 4/1971 | United Kingdom | 260/397.45 |

OTHER PUBLICATIONS

*Chem. Abstracts* vol. 68, 1968 pars. 69,177j, relied on.
Merck Index (1960) p. 462, relied on.

*Primary Examiner*—Elbert L. Roberts
*Attorney, Agent, or Firm*—Fidelman, Wolffe & Waldron

[57] ABSTRACT

A procedure for converting steroids characterized by presence of an 11βOH group into potent corticoids having one or more substituents, such as 6αF, 16α, 17α-hydroxy or isopropylidene dioxy, 16α or 16β methyl, Δ$^{1,4}$; by reacting the 11β-hydroxy steroid with trichloromethyl siloxane steroid, thereby rendering the normally sensitive 11 substituent inert to the series of reactions which thereafter incorporate one or more of the desired above listed substituents into the steroid molecule. The siloxy group is then hydrolyzed to regenerate the 11β-hydroxy substituent.

Many of the trimethyl siloxy steroids are novel compounds.

The siloxane may be selectively cleaved by reaction of the finely divided steroid with 40–60% aqueous HF.

18 Claims, 4 Drawing Figures

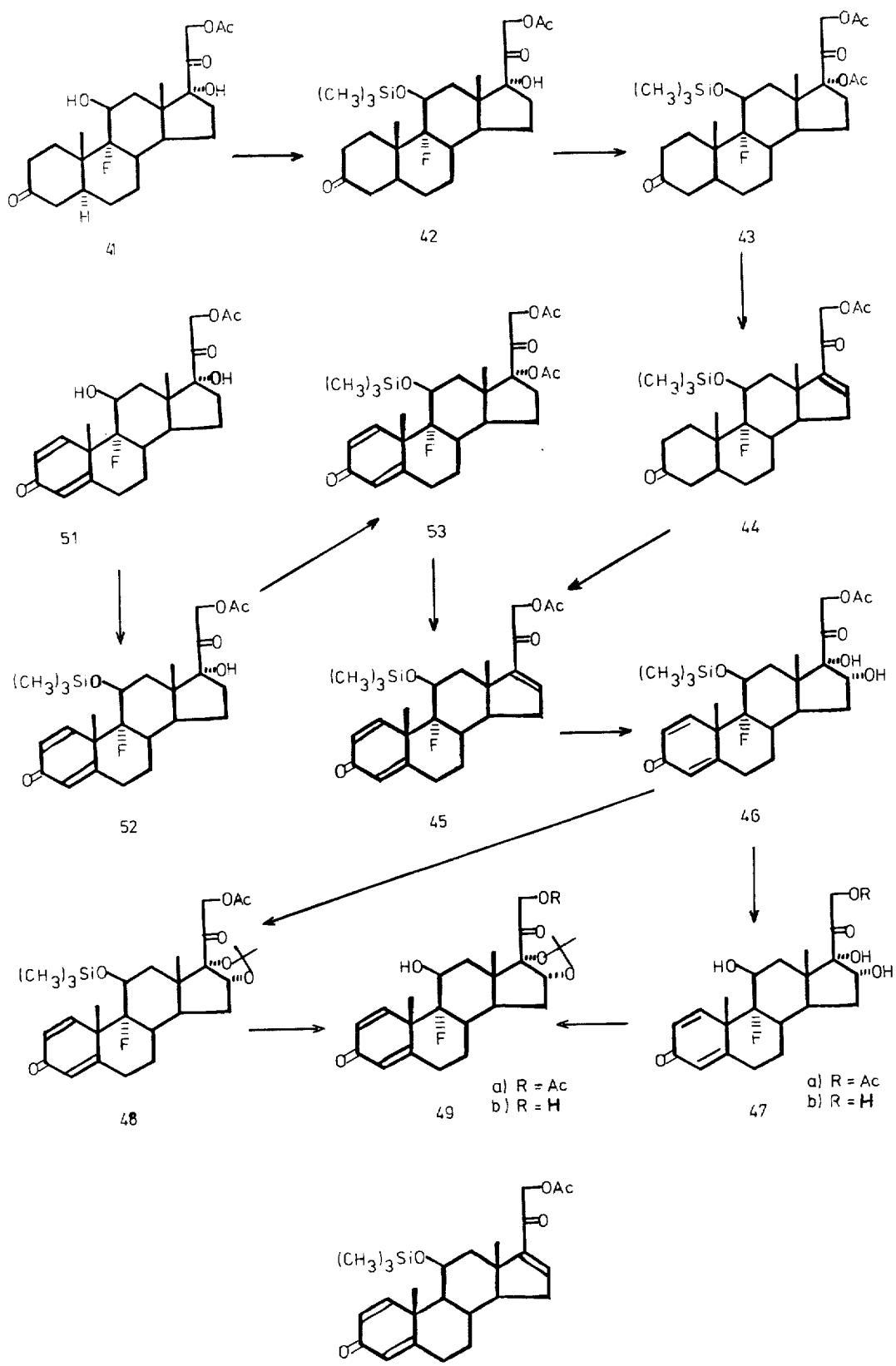

TRIMETHYL SILOXANE STEROID INTERMEDIATES

INTRODUCTION

Steroids characterized by presence of an 11β-hydroxy substituent are widely employed in the pharmaceutical arts, including for example dexamethasone, betamethasone, flucortilone, triamcinolone and many other potent anti-inflammatories. However, once the 11β-hydroxy substituent is present in a steroid molecule, its presence complicates transformation of that steroid into many of the desired pharmaceutically active compounds. In fact, many synthesis procedures which are high yielding conversion sequences for pregnane series steroids cannot be employed on a large scale with cortico-steroids. This situation has been one factor which heretofore has caused workers in the art to prefer diosgenin rather than hecogenin as source material for many cortico-steroids. However, an ever growing unavailability of diosgenin is forcing renewed consideration of hecogenin (a by-product from sisal cultivation) as source material for preparation of potent cortico-steroids.

One instance of such attention can be found in U.S. Pat. No. 3,876,633, wherein preparation of many corticoids from hecogenin are described, the sequences disclosed there proceeding by way of 3β-acyloxy-5α-pregna-9(11), 16-dien-20-one.

It has now been discovered that efficient conversion sequences are possible even when the 11β-hydroxy substituent (also present in the final cortico-steroid products) is on the molecule at the earliest stages of the conversion sequence.

Briefly stated, the present invention involves conduct of synthesis procedures on 11β-OH steroids while the 11 position is blocked off by a trimethyl siloxy group, i.e. 11β—O—Si(CH$_3$)$_3$. It has been discovered that the trimethyl siloxy group can be added and removed, selectively and quantitatively. It has also been discovered that presence of this blocking group is advantageous for reaction sequences that transform the steroid molecule and place therein one or more of the following groups: 6αF; 16,17-OH; 16α-CH$_3$, Δ$^{1,4}$.

A convenient starting compound for practice of the present invention is hydrocortisone itself or its 21-acetate, and in this connection it may be noted that British Pat. No. 1,227,992 discloses the formation of 11β—O—Si(CH$_3$)$_3$ hydrocortisone acetate by reacting hydrocortisone acetate with trimethyl chlorosilane in pyridine solution. The British patent suggests that the 17α OH position can then be esterified, after which the 11β hydroxy is reconstituted. However, the British patentees do not appear to have appreciated that use of the trimethyl siloxy blocking group might be advantageous in multi-step synthesis sequences leading to more active compounds than hydrocortisone esters, or to synthesis sequences for active compounds which do not proceed through hydrocortisone (as an intermediate).

BRIEF DESCRIPTION OF THE INVENTION

The present invention relates to a group of reaction sequences made feasible by forming an 11β—O—Si(CH$_3$)$_3$ derivative of certain intermediates. Individual conversion reactions known to be effective can then be employed on the 11β—O—Si(CH$_3$)$_3$ compounds including notably:

i. converting a 3-keto-4-ene steroid to the corresponding 3-acetoxy-4,6-diene steroid;
ii. reacting a 3-acetoxy-4,6-diene steroid with perchloryl fluoride to form the 3-keto-4-ene-6-F steroid;
iii. formation of a 16-ene steroid through elimination of a 17α-acetoxy substituent;
iv. permanganate oxidation of a 16-ene steroid to form the corresponding 16αOH, 17αOH steroid;
v. DDQ dehydrogenation to form a 1,4-diene;
vi. conversion of a 16-ene steroid to the corresponding 16α methyl steroid.

These various reactions are employed in advantageous sequences which lead to converting an 11 β-hydroxy steroid into one with one or more of the folllowng substituents thereon: 6αF; 16αOH,17αOH; 16αCH$_3$;Δ$^{1,4}$.

In all fairness, it is noted that not each reaction is superior (on a step-by-step comparison to a comparable reaction in the prior art sequences) but the sequences herein described are considered advantageous as a whole. In particular the reaction sequence of this invention permit facile conversion of hecogenin derived intermediates into potent corticoids having one or more the above listed substituents therein.

An important aspect of this invention is selective hydrolysis of trimethyl siloxanes through reaction with 40-60% aqueous HF.

DETAILED DESCRIPTION OF THE INVENTION

For understanding of the practice of this invention reference is made to the drawing illustration of reaction sequences wherein:

FIG. 4 illustrates how different source compounds may be converted into triamcinolone and its derivatives.

The 11β-trimethyl siloxanes employed for practice of this invention are formed by reacting the corresponding 11β-OH steroid with trimethyl chlorosilane in pyridine solution. Formation of the 11-β silyl ether of hydrocortisone (compound 1, FIG. 1) is known to the art (c.f. British Pat. 1,227,992). The British patent discloses that the silylation does not change the 17αOH group, and that (within limits ) the 11β—O—Si(Me)$_3$ group is inert to the strong acetylating conditions required to acetylate the 17αOH.

Figure 1:
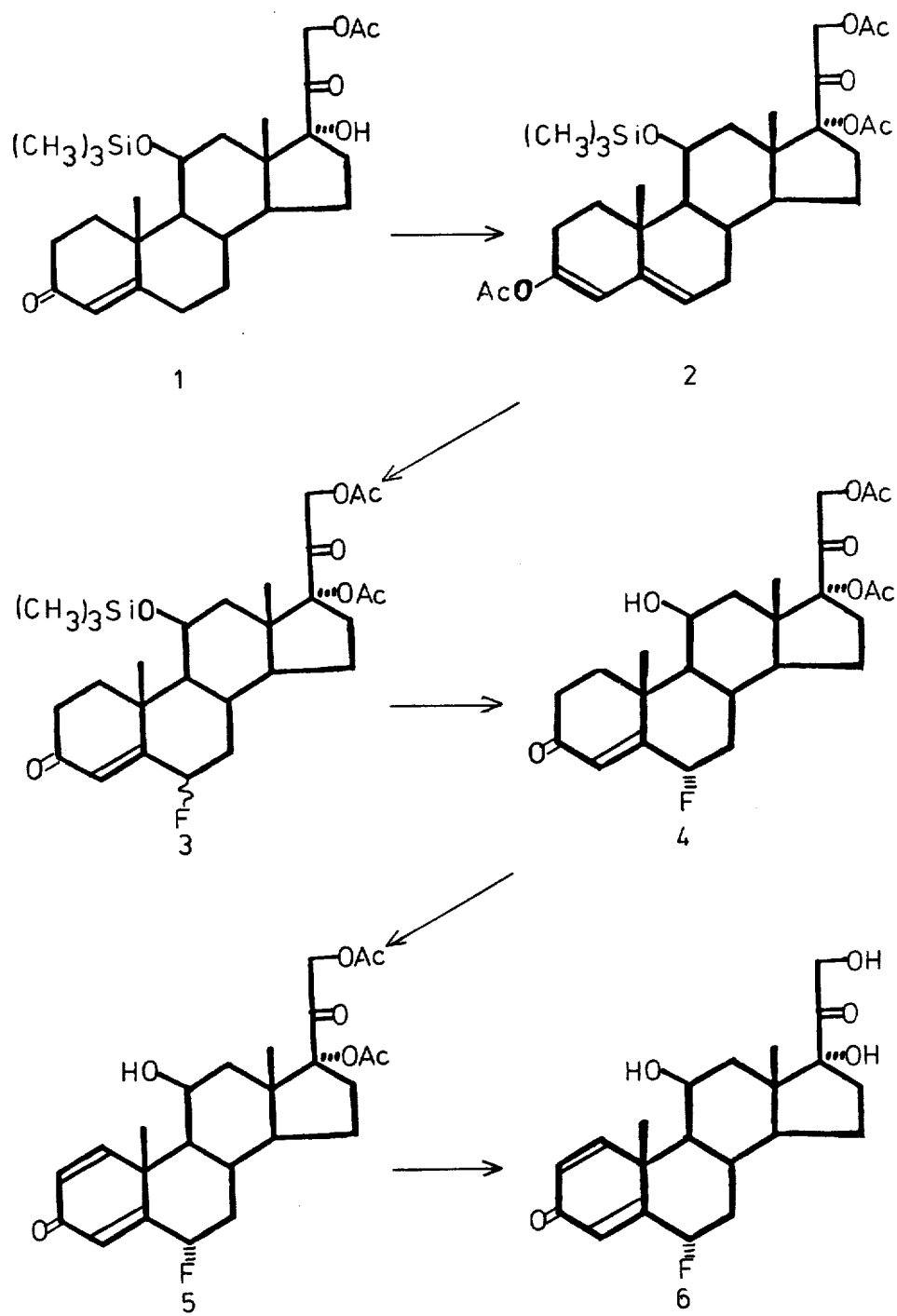
FIG. 1 illustrates the conversion of hydrocortisone to fluprednisolone.

As indicated above, it has now been found that the 11β trimethyl siloxy group is also stable against the conditions employed for enolizing steroids, and for fluorinating. FIG. 1 illustrates conversion of hydrocortisone to fluprednisolone.

Referring now to FIG. 1, it may be seen that subjecting the silyl ether of hydrocortisone 21-acetate (compound 1) to strong enolizong conditions forms, thereby, the enol acetate (compound 2 Thereafter reacting the enol acetate with perchloryl fluoride forms the 6-fluoro-Δ$^4$-3-keto-11β-trimethyl-siloxy (compound 3). Unexpectedly, the ratio of the 6α/6β fluoro in the product was found to be about 1:1. When the same enolizing and fluorinating reaction sequence is carried out on 11-desoxy steroids essentially 100% of the 6β-fluoro steroid is formed. Normally a separate acid catalyzed isomerization is then employed to convert the steroid to the 6αF configuration.

According to preferred practice of this invention, the blocking silyl group is thereafter removed by acid catalyzed methanolysis, regenerating the 11β-hydroxyl group and concommitantly isomerizing the 50—50 epimer mixture entirely to the 6αF configuration of 6α-Fluoro hydrocortisone 17,21-diacetate (compound 4).

The 6αfluoro hydrocortisone 17,21-diacetate is then dehydrogenated with DDQ (2,3-dichloro-4,5-dicyanobenzoquinone) to 6α fluoroprednisolone, 17α,21-diacetate (compound 5) which in turn is saponified to fluprednisolone (compound 6).

Figure 2:
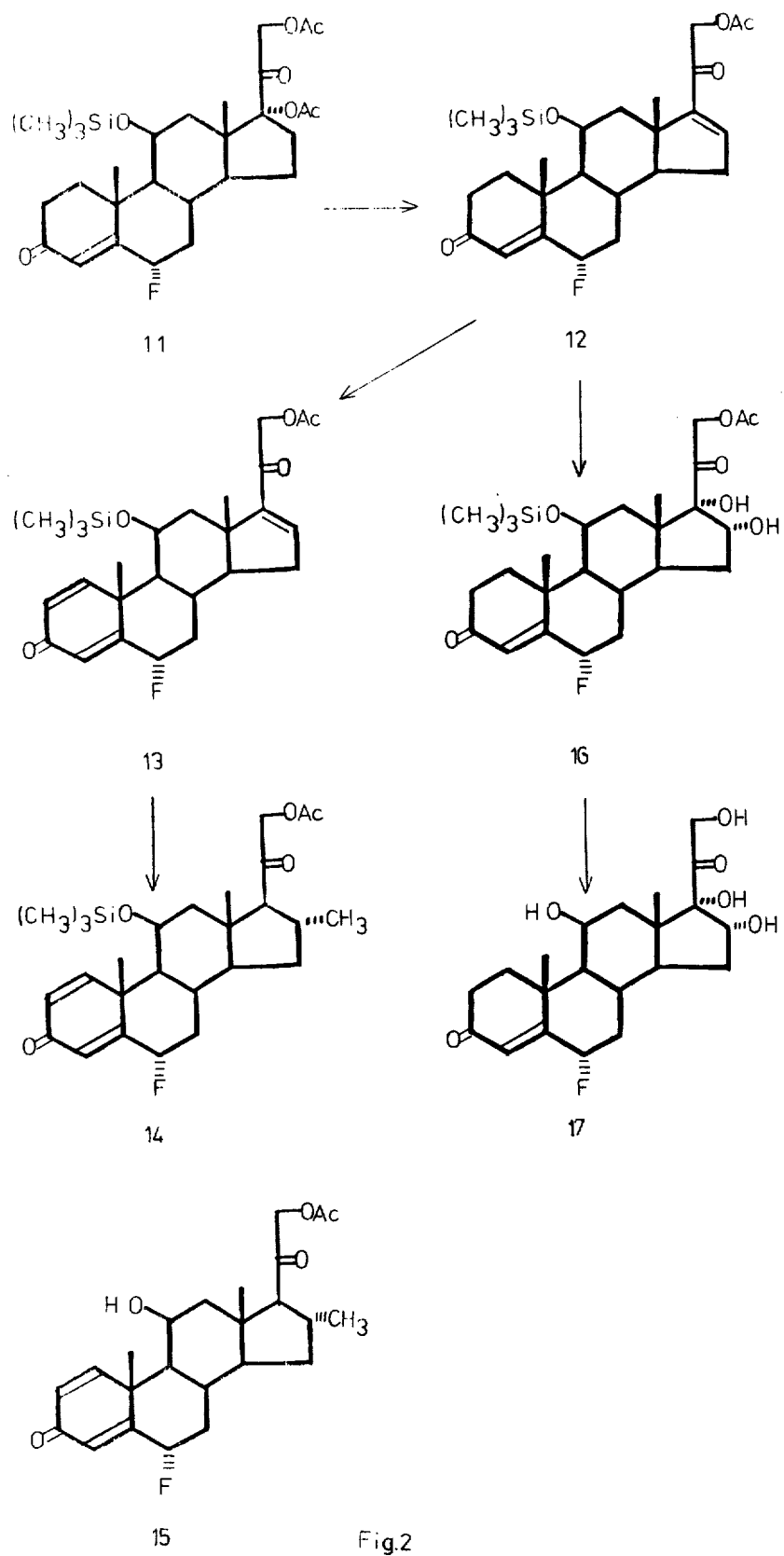
FIG. 2 illustrates a conversion to fluocortilone acetate and the fluandrenolone.

Referring now to FIG. 2, whereon is illustrated the reaction sequence preparing fluocortilone, the starting compound 11 is prepared by silylating 6α-fluoro hydrocortisone 17α,21-diacetate (compound 4). Thereafter the 17αOH is eliminated (by reaction with potassium acetate is dimethylformamide) to produce the $\Delta^{16}$-steroid (compound 12) in excellent yield. Dehydrogenation with DDQ forms the triene (compound 13). The trimethyl siloxy blocking group is inert to the elimination reaction conditions and to the DDQ dehydrogenation conditions. In addition the silyl blocking group has been found to be inert to the reaction with lithium-dimetyl-copper- employed to introduce the 16α methyl group (compound 14). This alkylation reaction is known for other 16-ene-20-keto steroids (R. Philippson, B. Acksteiner, P.E. Schulze, Offenlegungschrift 2,230,287, filed June 16, 1972). When the silyl blocking group is hydrolyzed from compound 14, fluocortilone (compound 15) is obtained.

FIG. 2 also illstrates conversion of the 16-ene (compound 12) to fluorandrenolone. Subjecting the 16-ene to potassium permanganate in a tube reactor resulted in the 16α,17α diol (compound 16) with the 11β silyl blocking group remaining intact. Acid hydrolysis of the blocking group and saponification of the 21 ester resulted in the tetrol compound 17 (fluorandrenolone), which in turn may be made into Cordran by known esterification procedures.

The reaction sequence illustrated in FIGS. 1 and 2 involve conversions which incorporate into an 11β hydroxy steroid one or more of the following groups: 6αF, 16α,17αhydroxy, 16α methyl, $\Delta^{1,4}$. Other reaction sequences hereinafter illustrated involve incorporation of 16α,17α isopropylidenedioxy and 16β methyl groups.

The inertness of the trimethyl silyl ether blocking group to the individual reactions involved is desirable, since mostly, reactions of choice are employed. Heretofore presence of and 11β-hydroxy group on the intermediate has precluded (commercial scale) utilization of what are believed to be the best reaction sequences for introducing the above listed functional groups into the readily available 11β-OH steroids such as hydrocortisone and hecogenin derived intermediates.

Thus with specific regard to introduction of the 6 F group on steroid molecules (illstrated in FIG. 1), the best reaction sequence is believed start with a $\Delta^4$-3 ketone, and:

i. form the $\Delta^{3,5}$ enol acetate;
ii. react with perchloryl fluoride to form the 6F derivative;
iii. isomerize to the 6α F configuration The above direct and efficient pathway is not feasible with steroids containing an 11β-hydroxy group. The 11β-OH is coacetylated during the conditions used for forming the $\Delta^{3,5}$ enol acetate. As a rule, a 11β-acetoxy group cannot be hydrolyzed successfully, for which reason many important products containing the 6α-fluoro-11α-hydroxy groupings (fluprednisolone, fluorandrenolide, flucortolone) have not been obtained from hydrocortisone by the direct efficient method referred to above. Protection of 11β-hydroxyl groups by the trimethylsilyl ether derivative now makes many important 6αsteroid products available from hydrocortisone via a simple and efficient pathway.

In carrying out the conversions illustrated in FIGS. 1 and 2 certain process advantages were observed:

I. Formation of the enol acetate and 17α-acetate.

While it is known that the 17α-hydroxy group of the 11β trimethyl siloxane blocked hydrocortisone 21-acetate can be acetylated (the BP 1,227,992 referred to above) without undesirable reaction about the 11β-trimethylsiloxy group, it was, perhaps, surprising that the much stronger reaction conditions of isopropenyl acetate and presence of 10 times as much paratoluenesulfonic acid catalyst would give the enol acetate trimethylsilyl ether (compound 2) in close to quantitative yield.

ii. Fluorination of the enol acetate with perchlorylfluoride.

Mention has already been made that the immediate reaction product of the enol acetate with $FClO_3$ (compound 3)exhibited the 6αF/6β epimeric ratio of about 1:1 according the TLC analysis. The like reaction on steroids with either no 11β substituent, or with one of small bulk results in up to 100% 6βF. The αF preference found to exist may be due to shielding of the β-side of the molecule from attack. Whatever the reason for the more favorable 6α/6βF ratio, the desirable consequence is that a cumbersome isomerization reaction step employed to convert the 6ξ-fluoro epimeric mixture of the steroid to the desired 6α-epimer can be avoided (as a separate step). Conversion of the epimeric mixture resulting from the fluorination (compound 3) to 6αF-epimer takes place concomitant with the acid catalyzed methanolysis employed to regenerate the 11β-hydroxy group and produce compound 4. Such favorable kinetics is of value to a large scale process sequence. The fluoro atom is small, and low energy differential exists between steroid 6α and 6β fluoro epimers. For that reason the usual isomerization reaction carried out is slow, stops at some sort of equilibrium, and mother liquor material rich in 6α-fluoro is recycled back to the isomerization reaction. Starting with a 50—50 epimeric mixture constitutes a considerable advantage, particularly when isomerization is made to occur during hydrolytic regeneration of the 11β-OH group.

iii. Dehydrogenation reaction with DDQ.

When a 2,3-dichloro-4,5-dicyanobenzoquinone dehydrogenation is run on an 11β-hydroxy steroid under the usual conditions (dioxane, sometimes with added acids) employed to favor production of the 1,4-dienoic-3-keto structure, some coreaction about the 11β-hydroxy occurs. The nature of this side reaction is not known, but is thought to be a dehydration at C-11 and C-12 leading to an enol which is rearranged to an 11-keto artifact.

In particular, inferior performance occurs if a negative group such as F is attached to C-9. For example 11β-hydroxy-9α-fluoro is not a good substrate for introduction of the 1,4-dien-3-keto system. However, when the 11-hydroxy group has been converted to the trimethylsilyl ether group, the side reaction of DDQ dehydration (leading to formation of an 11-keto artifact) is completely inhibited. A substantial improvement occures in the reaction yield for 9α-fluoro derivatives which is important to synthesis of such products as betamethasone and dexamethasone. It is not known whether the improvement is related to an inability to form the 11-keto, or to the generally more favorable ionics about the C-9 and C-11 positions. It may be noted that a $\Delta^4$-3-ketone converts to the 1,4-dien with DDQ in better yield than does a 5α-pregnane-3-ketone.

iv. Introduction of the 16-double bond. The trimethylsiloxy blocking group was inert to the usual conditions of eliminating the 17α -acetoxy group to form the 16-double bond (L. Salce, G. Hazen, E. Schoenewaldt, J. Org. Chem., 35, 1681 (1970). These conditions, i.e. potassium acetate in dimethylformamide at 110°–120° C, gave excellent conversion of compound 11 to 12, probably because of unique solubility properties of the silyl ether intermediate in the solvent combination used for trituration, permitting facile isolation of a pure product without loss of material in the mother liquors.

v. Hydroxylation of the 16-double bond.

Introduction of the 16α, and 17α dihydroxy groups, e.g. conversion of compound 12 to 16, is a very important aspect of the synthesis of certain corticoids (e.g. Triamcinolone, Fluocinolone). These groups form acetals with acetone very easily. The so called acetonides are themselves important corticoids. For carrying out the hydroxylation reaction of the 16-double bond, potassium permanganate is the reagent of choice (to react with the $\Delta^{16}$-steroid dissolved in acetone). The trimethylsiloxy blocking group was found to be inert to this reagent even in the presence of added acids such as formic acid so long as short time contact period is provided for the steroid solution with the acid containing permanganate solution, e.g. a tube reactor, 3 second contact time, with the reaction product continuously quenched by running into a large reservoir of aqueous sodium sulfite or bisulfite, which serves to keep the pH about neutral; manganese dioxide precipitates out.

vi. Formation of the acetonide.

Although the reaction to form the acetonide derivative of the 16α, 17α -diol is an acid catalyzed reaction (perchloric acid), it may be carried out before removing the silyl blocking group, since no co-reaction takes place about the silyl blocking group. Acetone is the reaction milieu and there is not enough water around to bring about the hydrolysis of the silyl blocking group. The solubility and crystallizing ability of the 11-trimethylsiloxy-16,17-acetonide products are favorable properties resulting in maximal yield and purity of the product.

vii. Methylation with lithium-dimethyl-copper.

It was found possible to apply the methylation procedure described in Deutsches Patentamt Offenlegungsschrift 2,230,287 (by R. Philippson and coworkers, June 16, 1972) to the 16-ene, 11β-trimethylsiloxy compound 13 without concomitant loss of the blocking group to produce the 16α methyl steroid of compound 14. As an advantage over the process described by the German workers, it was found not necessary to reacetylate during the workup, indicating a shielding of the β-side of the steroid molecule by the bulky trimethylsiloxy group. The 16αmethyl,11β-trimethylsiloxy compound 14 exhibited superior crystallization and solubility characteristics, as did all of the 11β-trimethylsiloxy derivatives.

viii. Regeneration of the 11β-hydroxy group.

It is essential for practice of this invention to appreciate limits to the stability of the trimethylsiloxy ethers during the course of the intended reactions (so as to avoid any undesired cleavage of the silyl ether resulting in equally undesired coreaction of the 11-hydroxy functions). It is of course important for practice of this invention to possess selective methods for regeneration of the 11β-hydroxy function, after the intended reactions have been successfully carried out. Without a dependable selective procedure capable of quantitatively cleaving the siloxy group with no co-reaction at other sensitive points on the steroid molecule, the 11β-trimethylsiloxy ethers would be of limited use as reaction intermediates. Unfortunately, previously known cleavage reactions adapted to remove the siloxy group were unsatisfactory in many instances. Fortunately, the trimethylsiloxy blocking group was found to be sufficiently stable to carry out all the reactions discussed above. However, in some instances the usual reaction conditions were modified. For instance (Example 1 below) acetylation of the hindered 17α-hydroxy function has been achieved concomitantly with enolization of the $\Delta^4$-3-keto moiety to the $\Delta^{4,5}$ diene without any transacetylation at C-11 by using the isopropenyl acetate/paratoluenesulfonic acid reagent, but a conventional workup after 17α-acetylation with the usual acetic anhydride/paratoluenesulfonic acid reagent, (Example 21 below) could not be employed. Resort was had to a dimethyl formamide, sodium acetate buffer, to avoid cleavage of the silyl blocking group.

As a whole it has been found that the rate of formation and the stability of the silyl ether blocking group was dependent upon the substituent in the 9α-position and on whether ring A was a 1,4-diene-3-one, a 4-en-3-one or a saturated 5αH-3-one. Conditions which were suitable for acetylation of the 17α-hydroxy group in the 9α-fluoro series, caused acetolysis at the trimethylsiloxy blocking group in the prednisolone series (1,4-diene-3-one).

An important additional aspect of this invention is the discovery of a novel cleavage method, which briefly is to expose the 11β-trimethyl-siloxy ether to 40–60%, aqueous hydrofluoric acid, at room temperature, and preferably about 47–50%.

This cleavage reaction cannot be explained. It is heterogeneous (the steroid reactant is in suspension). The reaction is fast and requires small particle size. The reaction may be controlled by TLC in a small pilot run of the same material and acid, and letting the reaction run until just under 100%, e.g. about 95%, of the starting material has reacted. If the cleavage reaction is run longer, other reaction products are formed. The total material is filtered off from a neutralized aqueous suspension, and for some uses of the steroid hydrolysis product no recrystallization is necessary. (As may be seen from Examples 10, 12, 16, 19 and 27 below there are differences in reaction time for complete cleavage). The cleavage reaction is very specific. One demonstration of the specificity of this cleavage reaction is that hydrolysis of compound 3 with HF, cleaved off the silyl blocking group but the 6αF/6βF ratio in the steroid product remained the same. A different cleavage reaction, i.e. HCl/chlf/Ethanol is required for combined cleavage and isomerization. The aqueous HF method of cleavage is however exceedingly satisfactory where specificity is desirable. Thus, very easily hydrolyzable 21-acetoxy groups, as well as 17,21-diacetoxy groups of 20-ketones are left completely intact by aqueous HF cleavage. Similarly 16,17-acetonide groups are left untouched when the cleavage contact time is kept to less than 100% completion, i.e. neutralize when 95+% of the starting material has been shown reacted by TLC test on the pilot run.

Figure 3:
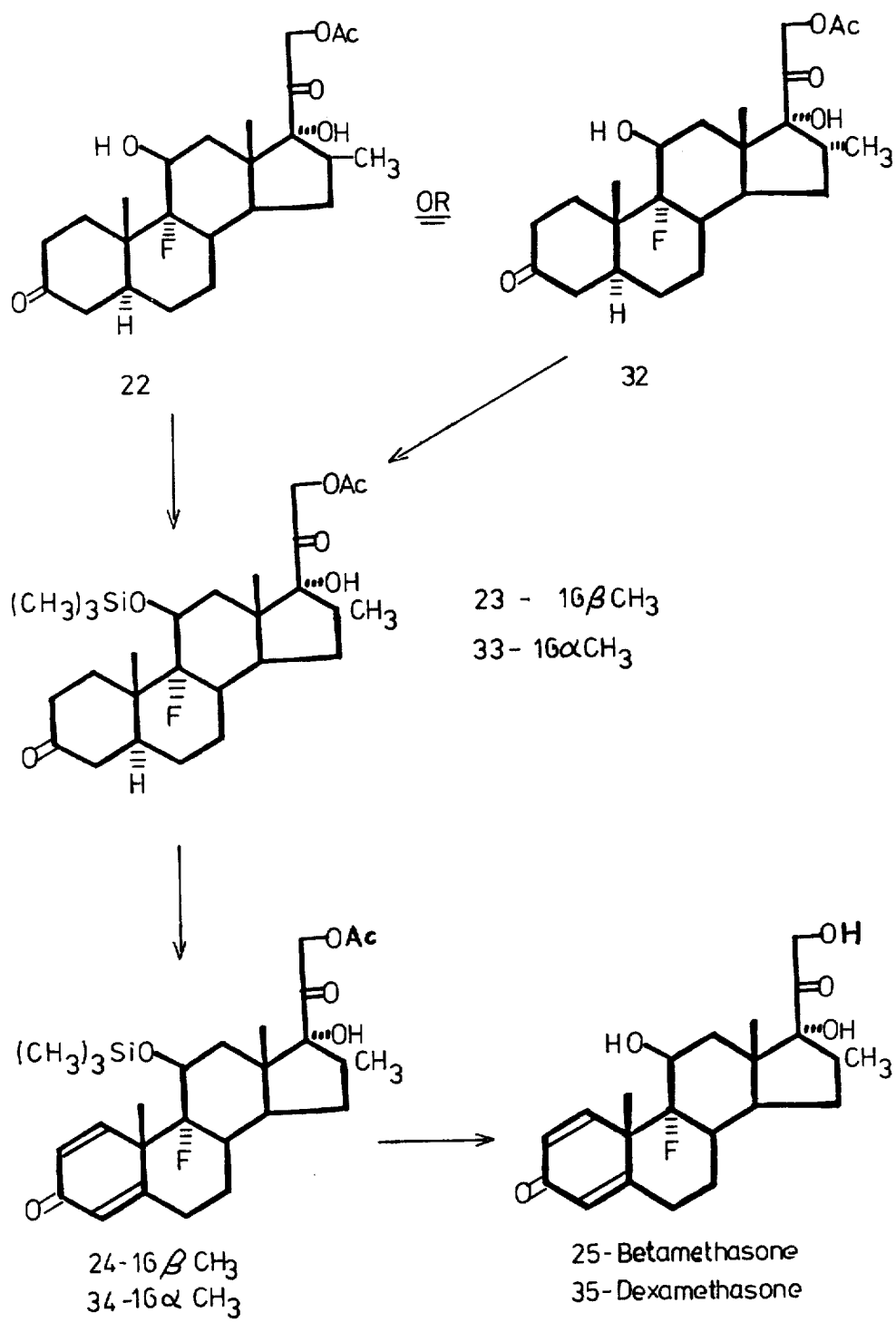
FIG. 3 illustrates a conversion to betamethasone or dexamethasone.

Reference can now be made to FIGS. 3 and 4 for further illustrations of practice of this invention. These figures show how the already described reactions have been combined into reaction sequences well adapted to synthesis of widely used corticoids, and moreover, illustrate how hecogenin derived intermediates may be employed as starting materials, such intermediates generally being characterized by presence of saturated rings A and B connected trans (i.e. 5αH).

As is shown in FIG. 3, compound 22 (tetrahydrobetamethasone) is silylated to form the 11β trimethyl siloxane, compound 23. Then dehydrogenation with 2,3-dichloro-4,5-dicyanobenzoquinone (DDQ) in dioxane solution provides the 1,4-dien, compound 24. Thereafter aqueous HF hydrolytic cleavage forms betamethasone, compound 25.

In a comparable sequence, also shown in FIG. 3, the 16 methyl fluorohydrin, compound 32 is transformed into the silyl ether, compound 33, then DDQ dehydrogenated to the $\Delta^{1,4}$-dien, compound 34, and thereafter hydrolyzed to dexamethasone, compound 35.

Still another area of practice of this invention is production of triamcinolone from either hecogenin, or from prednisolone. FIG. 4 illustrates the reaction sequences involved.

One starting compound 41 is 11β,17α-dihydroxy-21-acetoxy-9α-fluoro-5α-pregnane-3,20-dione, a compound reported by J. Elks, G.H. Phillipps, W.F. Wall; J. Chem. Soc. 1958, 4001. This compound is converted into the trimethyl silyl ether, compound 42, then the 17αhydroxy group is acetylated to form compound 43 using conditions so that no enol acetate formation occurs around the 3-keto group. Thereafter the 17α,21-diacetate is subjected to a potassium acetate in dimethyl formamide elimination reaction to introduce the 16-double bond (efficiently), forming compound 44. The 1,4-diene system was obtained by dehydrogenation with DDQ, forming compound 45.

Compound 45 is converted to the 16α,17α diol, compound 46 by short time, e.g. three seconds, tube reactor contact with potassium permanganate. In turn compound 46 can be hydrolyzed to either of compounds 47 (i.e. 21-acetoxy or 21-hydroxy) or reacted with acetone to arrive at the acetonide of compound 48, which in turn may be hydrolyzed to form either the 21-acetoxy or 21-hydroxy of compounds 49. The two compounds 47 can be reacted with acetone to form appropriately the acetonide of compound 49a or 49b.

Alternatively compounds 49 can be arrived at from prednisolone by first converting prenisolone, 21-acetate to the 11β, 9α fluorohydrin thereof, compound 51, then silylating the 11β-OH to form compound 52, followed by acetylating the 17α OH steroid to form the 17α acetoxy compound 53, followed by elimination of the 17α acetoxy group (potassium acetate in dimethyl formamide) to form the 16-ene compound 45, then proceeding to compounds 47 to 49 as already described.

The same sequence of reactions (i.e. of compounds 51 to 45) can be employed directly on prednisolone, 21-acetate to produce compound 55 (FIG. 4) and the compound 45–49 sequence already described then employed to form prednacinolide or its 21-acetate.

For further understanding of the present invention, the following specific examples thereof are presented.

EXAMPLE 1

A mixture of 22g of 11β-trimethyl-siloxy-17α-hydroxy-21-acetoxy-pregn-4-ene-3,20-dione, compound 1 in FIG. 1 (prepared according to J. Lens, A.F. Marx, BP 1,227,992 of Apr. 15, 1971, Example III), 2.2g of p-toluenesulfonic acid monohydrate, and 88 ml of isopropenyl acetate was heated under reflux for a period of 1.5 hr, and cooled. Then 3 g of anhydrous sodium acetate was added and the reaction mixture diluted with 140 ml of methylisobutyl ketone. The supernatant was decanted from the salt crystals and the resulting solution was washed twice, each time with 200 ml of water, then once with 200 ml of saturated aqueous sodium chloride solution, dried over anhydrous sodium sulphate, and evaporated under reduced pressure to a semi-crystalline residue. This residue can be dried to constant weight at 40° C/20 mm of Hg then employed for starting material for later conversions. From the residue pure 11β-trimethylsiloxy-3,17α,21-triacetoxy-pregna-3,5-diene-20-one (compound 2) can be prepared in the following manner:

The residue was dissolved in the minimum amount of benzene and charged on a column of silica gel. The product was eluted with benzene/ ethylacetate (19:1), and gave a crystalline residue, which upon trituration with methaol containing a trace of pyridine gave the pure enol acetate with melting point about 148°–160° C.
IR: 1760, 1740, 1240, 1070, 845 cm$^{-1}$

EXAMPLE 2

To a solution of 26 g of the enol acetate residue described in Example 1 (11β-trimethyl-siloxy-3,17α,21-triacetoxy pregna-3,5-diene-20-one) in 400 ml acetone was added a solution of 10 g of anhydrous potassium acetate in 240 ml of absolute ethanol. The resulting solution was cooled to −30° treated with a stream of perchloryl fluoride for 1 hr, maintaining the temperature within the range −30° to −20°. The reaction mixture was maintained within this temperature range for 60 hours, and then precipitated by pouring into 8 liters of iced water containing 20 g sodium sulphite. After 1 hr. standing the fine precipitate was collected, washed with water and dried under vacuum to constant weight (22g). A thin layer chromatographic study (benzene-ether 7:3) showed the presence of two products in about equal amounts, which were identified as the 6α- and 6β-epimeric pair of compound 3 (i.e. 11β-trimethyl-siloxy-17α,21-diacetoxy-6α-fluoro-pregn -4-ene-3,20-dione).

EXAMPLE 3

24 g of the 6αβ-epimeric mixture product described in Example 2 was dissolved in 1.2 liters of chloroform (which the supplier had stabilized by the addition of 0.6% ethanol). This solution was cooled to −40° C, saturated with anhydrous hydrogen chloride, and maintained at −30° for a period of 2 hours. The solution was then washed with water (3 liters) and with 1 litre of aqueous saturated sodium chloride solution, dried over anhydrous sodium sulphate, and evaporated to dryness under reduced pressure. The crystalline product, compound 4, (i.e. 11β-hydroxy-17α,21-diacetoxy-6α-fluoro-pregn -4-ene-3,20-dione) was obtained from ethyl acetate.

m.p.: about 231°–234° C; optical rotation not taken.

Salient bands IR: 3520, 1750, 1730, 1670, 1620, 1240 cm$^{-1}$

EXAMPLE 4

A mixture of 3 g of 11β-hydroxy-17α,21-diacetoxy-6α-fluoro-pregn4-ene-3,20-dione [compound 4, the product of Example 3]., 2.5 g of 2,3-dichloro-4,5-dicyanobenzoquinone, and 30 ml of dioxan was heated under reflux for 2 hours. The resulting dark colored suspension was cooled, filtered from dichlorodicyanohydroquinone, and then evaporated to dryness. The residue so obtained was dissolved in chloroform and filtered through neutral alumina (50 g). The solvent was evaporated under reduced pressure. The residue crystallized from methanol as colorless prisms, m.p.: 235°–240°,λmax, 241 nm ($\epsilon$= 14,200). The analytical sample of 11β-hydroxy-17α,21-diacetoxy-6α-fluoropregna-1,4-diene-3,20-dione (compound 5) was obtained by an additional recrystallization from methanol.

This product of Example 4 can be converted into fluoprednisolone according to the following procedure (Bjarte Loken and George Rosenkranz, U.S. Pat. No. 2,860,149, CA 91959, 14/1/57): To a suspension of 700 mg of this 17α,21-diacetate in 7 ml of the methanol while stirring under pure nitrogen at 23° was added a solution of 130 mg of anhydrous potassium carbonate in 1.5 ml of water (this solution had been boiled to remove oxygen and then cooled under pure nitrogen). The reaction mixture was stirred under a nitrogen atmosphere at 23°–25° for a period of 60 minutes. 2-3 drops of acetic acid was added and the agitation continued until carbon dioxide evolution stopped. The product was precipitated with water containing salt, the solids filtered, washed on the filter with water, collected and dried.

The weight of the crude product corresponded to slightly less than the quantitative yield. Recrystallization from acetone gave the pure triol of compound 6: 11β,17α,21-trihydroxy-6α-fluoro-pregna-1,4-diene-3,20-dione known as fluprednisolone M.P., 207°–210°, $[\alpha]_D$ + 92°.

EXAMPLE 5

To a solution of 7.0 g of 11β-hydroxy-17α,21-diacetoxy-6α-fluoro-pregn-4,ene-3,20-dione (compound 4) obtained according to Example 3, in 16 ml of dry pyridine was added 3 ml of trimethyl chlorosilane. This mixture was stirrred for 2 hours at room temperature and then diluted with 200 ml methyl isobutyl ketone, and 32 ml of 6N sulfuric acid was added with agitation and cooling. The mixture was allowed to solidify, the organic layer separated and washed successively with dilute sulfuric acid, 10% aqueous sodium bicarbonate and finally with water. Concentration to a small volume under reduced pressure gave a crystalline slurry from which the 11β-trimethylsiloxy-17α,21-diacetoxy-6α-fluoro-pregn-4-ene-3,20-dione (compound 11) could be collected.

Obtained: 8.05 g.

EXAMPLE 6

A mixture of 4.0 g of 11β-trimethylsiloxy-17α,21-diacetoxy-6α-fluoro-pregn-4,ene-3,20-dione (from Example 5) 2 g anhydrous potassium acetate and 10 dimethyl formamide was heated for a period of 4 hours at 110°–120° in an atmosphere of nitrogen. The reaction mixture was cooled and poured into 60 ml of water and ice. The solids were filtered after 2 hours of standing, washed on the filter with water and dried. Trituration of this material with acetone ether gave the 11β-trimethyl siloxy-21-acetoxy-6α-fluoro-pregna-4,16-diene-3,20-dione in a crystalline form weighing 3.5 g (compound 12). TLC spotting showed the substance to be homogenous.

EXAMPLE 7

A mixture of 3.5 g of 11β-trimethylsiloxy-21-acetoxy-6α-fluoropregna-4,16-diene-3,20-dione obtained according to Example 6, 2.65 g of 2,3-dichloro-4,5-dicyanobenzoquinone (DDQ) and 30 ml of dioxan was heated under reflux for 2 hours. The resulting dark colored suspension was cooled, filtered from dichlorodicyanohydroquinone, and evaporated to dryness. The residue was dissolved in chloroform and passed through a short column of neutral alumina (50 g). The solvent was evaporated under reduced pressure. The residue was crystallized from methanol. The analytical sample of 11β-trimethylsiloxy-21-acetoxy-6α-fluoropregna-1,4,16-triene-3,20-dione (compound 13) was obtained by an additional recrystallization from methanol. The yield was 2.65 g.

EXAMPLE 8

750 mg cuprous iodide was suspended in 10 ml dichloromethane in an atmosphere of nitrogen and cooled to −10° C. To this suspension under stirring and cooling was added 9 ml of a 2% solution of lithium-methyl by drop wise addition maintaining the temperature below −5°. To the so obtained lithium-dimethyl-copper solution was added 425 mg 11β-trimethylsiloxy-21-acetoxy-6α-fluoropregna-1,4,16-triene-3,20-dione obtained according to Example 8 dissolved in 3 ml dichloromethane. The temperature of the reaction mixture was kept below −1°, and the stirring was maintained for a period of 15 minutes. The reaction mixture was poured into an aqueous ammonium chloride solution, the organic phase separated and the aqueous phase re-extracted with dichloromethane. The organic extracts were combined, washed with water, dried over anhydrous sodium sulfate and concentrated to dryness under reduced pressure. Trituration with acetone afforded a crystalline product 11β-trimethylsiloxy-21-acetoxy-6α-fluoro-16α-methyl-pregna-1,4-diene-3,20-dione (compound 14) yield 320 mg TLC: homogeneous.

EXAMPLE 9

1 g of 11β-trimethylsiloxy-21-acetoxy-6α-fluoro-16α-methylpregna-1,4-diene-3,20-dione obtained according to Example 8 was powdered finely and suspended in 10 ml of 49% aqueous hydrofluoric acid with stirring at 0°. After 5 minutes of contact about 5% of the starting material remained in a pilot experiment (by TLC, BPA). The reaction product was then neutralized by pouring into 12% sodium carbonate solution (200 ml), the solids were filtered, washed with water, collected, dried and recrystallized from acetone. There was obtained 600 mg of 11β-hydroxy-21-acetoxy-6αfluro-16α-methylpregna-1,4-diene-3,20-dione (compound 15). Fluocortilone—a well known anti-inflammatory corticosteroid—can be obtained by hydrolysis of compound 15 (ref: B. Loken, G. rosenkranz, U.S. Pat. No. 2,860,143, C.A. 91959, Jan. 14, 1957).

EXAMPLE 10

A solution of 200 g of 11β-trimethylsiloxy-21-acetoxy-6α-fluoro-pregna-4,16-diene-3,20-dione obtained according to Example 6 (compound 12) in a mixture of 40 liters acetone was charged into the holding tank of a tube reactor. In the other holding tank was charged a solution of 150 g potassium permanganate in 12.5 liter water, and 50 ml formic acid. With the help of the dosage pumps the two solutions were combined into the reaction tube at a feed rate of 80 and 25 1/hour respectively. The reactor tube was dimensioned so that the two solutions were in contact at $-5°$ for a period of 3 seconds with the reaction product flowing directly from the reaction tube into 10 liters of an aqueous sodium bisulfite solution containing 500 gms of sodium bisulfite (which stops the reaction). The suspension was filtered to remove manganese dioxide, the filtrate was concentrated under reduced pressure to about 2 liters and diluted with 2.5 liters of water. The crystalline slurry was left for 4 hours then filtered and the solids washed on the filter with water, collected and dried. Recrystallization from acetone/ether gave 190 g of purified 11$\beta$trimethylsiloxy-16$\alpha$,17$\alpha$-dihydroxy-21-acetoxy-6$\alpha$-fluoro-pregn-4-ene-3,20-dione (compound 16).

EXAMPLE 11

3.5 g of 11$\beta$-trimethylsiloxy-16$\alpha$,17$\alpha$-dihydroxy-21-acetoxy-6$\alpha$-fluoro pregn-4-ene-3,20-dione (from Example 10) was treated with 35 ml 49% aqueous hydrofluoric acid exactly as described in Example 9. Obtained was 11$\beta$,16$\alpha$,17$\alpha$-trihydroxy-21-acetoxy-6$\alpha$-fluoro-pregn-4-ene-3,20-dione, which after mild saponification gave 2.0 g of 11$\beta$,21,16$\alpha$,17$\alpha$-tetra-hydroxy-6$\alpha$-fluoro-pregn-4-ene-3,20-dione (compound 17), which is Flurandrenolone, a well known anti-inflammatory steroid. Reaction of this compound with acetone under acid catalysis according to known methods leads to formation of the 16,17-acetonide derivative (known as Cordran, Drenisone and Drocort).

EXAMPLE 12

When 7.0 of 11$\beta$,17$\alpha$-dihydroxy-21-acetoxy-9$\alpha$-fluoro-16$\alpha$-methyl-5$\alpha$-pregnane-3,20-dione, prepared according to Carrington et al J. Chem. Soc. 1961, 4560, was treated exactly as in Example 5 with trimethylchlorosilane in pyridine solution there was obtained 1.7 g of 11$\beta$-trimethylsiloxy-17$\alpha$-hydroxy-21-acetoxy-9$\alpha$-fluoro-16$\beta$-methyl-5$\alpha$-pregnane-3,20-dione (compound 23).

EXAMPLE 13

When 3.5 g of the product of Example 12 (11$\beta$-trimethylsiloxy-17$\alpha$-hydroxy21-acetoxy-9$\alpha$-fluoro-16$\beta$-methyl-5$\alpha$-pregnane-3,20-dione) was treated in all details as in Example 7 with 2.65 g of 2,3-dichloro-4,5-dicyanobenzoquinone in dioxane solution, there was obtained 1.7 g of 11$\beta$-trimethylsiloxy-17$\alpha$-hydroxy-21-acetoxy-9$\alpha$-fluoro-16$\beta$-methyl-pregna-1,4-diene-3,20-dione (compound 24).

EXAMPLE 14

To a slurry of 1.7 g of 11$\beta$-trimethylsiloxy-17$\alpha$-hydroxy-21-acetoxy-9$\alpha$-fluoro-16$\beta$-methyl-pregna-1,4-diene-3,20-dione (obtained according to Example 13) in 16 ml of methanol was slowly added a solution of 170 mg potassium hydroxide in 4 ml of methanol. This mixture was stirred in inert atmosphere at 10° for 1 hour. TLC check indicated that the starting material had disappeared and the more polar 21-hydroxy compound had been formed. The reaction product was poured into a large volume of water (450 ml), neutralized by addition of a little acetic acid, and most of the clear supenatant solution was decanted. The remaining slurry of solids was filtered the solids washed on the filter with abundant water, collected and dried. This resulting 21-hydroxy substance was powdered and treated with 48% aqueous hydrofluoric acid (17 ml) exactly as described in Example 10, but it took 8 minutes of contact until the starting material had disappeared. The crude water precipitated product was recrystallized from acetone and gave 1.2 g of 11$\beta$,17$\alpha$,21-trihydroxy-9$\alpha$-fluoro-16$\beta$-methylpregna-1,4-diene-3,20-dione (Betamethasone, a strong topical anti-inflammatory agent).

EXAMPLE 15

The starting material for Compound 32 ("tetrahydrodexamethasone acetate") is 17$\alpha$hydroxy-21-acetoxy-9$\beta$,11$\beta$-epoxy-16$\alpha$methyl-5$\alpha$-pregnane-3,20-dione, disclosed in patent 3,876,633 which may be prepared according to Example 20 of the patent. The steroid was reacted with a THF/HF complex prepared by absorbing 40 g of HF in 80 ml of tetrahydrofuran (precooled to $-30°$ C) at temperatures controlled to at least $-20°$ C.

10 g of the steroid was added to the fresh (cold) THF/HF complex and vigorous agitation was maintained while the temperature was permitted to climb to 0° C over a 2-3 hour period. The reaction mixture was maintained at 0° until TLC showed disappearance of the starting steroid.

The reacted complex was then poured into 800 ml of water containing 150 g of sodium acetate and 300 g of ice. The mixture was agitated at 0° -5° for several hours, then filtered, washed on the filter and dried. Recrystallization from ethyl acetate gave 8.5 g of pure 11$\beta$,17$\alpha$-dihydroxy-21-acetoxy-9$\alpha$-fluoro-16$\alpha$-methyl-5$\alpha$-pregnane-3,20-dione. When 7.0 g of "tetrahydro dexamethasone acetate", e.g. 11$\beta$,17$\alpha$-dihydroxy-21-acetoxy-9$\beta$-fluoro-16$\beta$-methyl-5$\alpha$-pregnane-3,20 -dione (compound 32) was treated exactly as in Example 5 with trimethylchlorosilane in pyridine solution, there was obtained 8.5 g of 11$\beta$-trimethylsiloxy-17$\alpha$hydroxy-21-acetoxy-9$\alpha$-fluoro-16$\alpha$-methyl-5$\alpha$-pregnane-3,20-dione (compound 33).

EXAMPLE 16

When 3.5 g of the (compound 33) product of Example 15 (11$\beta$-trimethylsiloxy-17$\alpha$hydroxy-21-acetoxy-9$\alpha$-fluoro-16$\alpha$-methyl5$\alpha$-pregnane-3,20-dione) was treated in all details as in Example 7 with 2.65 g of 2,3-dichloro-4,5-dicyanobenzoquinone in dioxane solution there was obtained 1.85 g of 11$\beta$-trimethylsiloxy-17$\alpha$hydroxy21-acetoxy-9$\alpha$-fluoro-16$\alpha$methyl-pregna-1,4-diene-3,20-dione (compound 34).

EXAMPLE 17

When 1.7 g of 11$\beta$-trimethylsiloxy-17$\alpha$-hydroxy-21-acetoxy-9$\alpha$-fluoro-16$\alpha$-methylpregna-1,4-diene-3,20-dione from Example 16 was treated exactly as described in Example 14, there was obtained 1.3 g of 11$\beta$,17$\alpha$,21-trihydroxy-9$\alpha$-fluoro-16$\alpha$-methyl-pregna-1,4-diene-3,20-dione (Dexamethasone, a strong topical anti-inflammatory agent).

EXAMPLE 18

To a solution of 7 g of 11$\beta$,17$\alpha$dihydroxy-21-acetoxy-9$\alpha$-fluoro-5$\alpha$-pregnane-3,20 -dione (which was prepared from hecogenin according to J. Elks, G. H. Phillipps and W. F. Wall: J. Chem. Soc., 1958, 4001) (Compound 41) in 16 ml of dry pyridine was added 3 ml of trimethyl chloriosilane. This mixture was treated in all details exactly as described in Example 5; there was obtained 8.11 g of 11β-trimethylsiloxy-17α-hydroxy-21-acetoxy9α-fluoro-5α-pregnane-3,20-dione (compound 42).

EXAMPLE 19

A mixture of 8 g of 11β-trimethylsiloxy-17αhydroxy-21-acetoxy-9αfluoro5αpregnane-3,20dione obtained according to Example 18, 16 ml of acetic anhydride and 150 mg paratoluenesulfonic acid was heated under stirring at 55°–70° for 45 min. The reaction mixture was cooled to about 35°–40°, 15 ml of dimethyl formamide and 3 ml of a 10% aqueous solution of sodium acetate added, and the temperature was controlled to remain below 45°–50°. Finally, the reaction mixture was poured into 350 ml of ice and water and a close to quantitative yield (8.65 g) of the diacetate (compound 43) was collected by filtration. The analytic sample of 11β-trimethylsiloxy-17α,21-diacetoxy9α-fluoro5α-pregnane-3,20-dione was obtained by recrystallization from dichloromethane-methanol.

EXAMPLE 20

A mixture of 8.0 g of 11β-trimethylsiloxy-17α,21-diacetoxy9αfluoro-5α-pregnane3,20-dione obtained according to Example 19, 4 g anhydrous potassium acetate and 20 ml of dimethyl formamide was heated for a period of 4 hours at 110°–120° in an atmosphere of nitrogen. The reaction mixture was cooled and poured into 120 ml of water and ice. The mixture was left stirring for 30 minutes, then lft standing for a period of 2 hours, filtered, washed on the filter with abundant water, collected and dried. Trituration of this crude product with acetone/ether gave 11β-trimethylsiloxy-21-acetoxy-9α-fluoro-5α-pregn-16-ene-3,20-dione (compound 44). Yield: 7.0 g.

EXAMPLE 21

When 3.5 g of the product of Example 20 (11βtrimethylsiloxy-21-acetoxy9α-fluoro-5α-pregn-16-ene-3,20-dione) was treated in all details as in Example 8 with 2.65 g of 2,3-dichloro 4,5-dicyanobenzoquinone in dioxane solution, there was obtained 2.0 g of 11β-trimethylsiloxy-21-acetoxy-9αfluoro-pregna-1,4,16-triene-3,20-dione (compound 45).

EXAMPLE 22

A solution of 11β-trimethylsiloxy-21-acetoxy-9α-fluor-pregna-1,4,16-triene-3,20-dione (1 g) from Example 21 (or from Example 28) in acetone (50 ml) and formic acid (1 ml) was cooled to 0° and mixed quickly with an ice-cold solution of potassium permanganate (0.7 g) in water (20 ml) and acetone (30 ml). After 5 seconds the reaction was quenched with a solution of sodium sulfite (1.5 g) in water (10 ml). The reaction mixture was filtered and the colorless filtrate was concentrated until no acetone remained. After 30 minutes standing, the precipitate was collected, washed with water and dried under vacuum. There was obtained 0.94 g of (compound 46) 11β-trimethylsiloxy-16α,17α-hydroxy-21-acetoxy-9α-fluoropregna-1,4-diene-3,20-dione. m.p. about 203° –204°; TLC, homogenous (BPA).

IR bands at 3450, 3400, 1760, 1630, 1615, 1260, 1240, 1080, 845 cm⁻¹.

Larger amounts of the 1,4,16-triene starting material is better treated in a tube reactor as described in Example 9.

EXAMPLE 23

0.94 g of 11β-trimethylsiloxy-21-acetoxy-9α-fluoropregna-1,4,16-triene-3,20-dione (from Example 22) in 10 ml 49% aqueous hydrofluoric acid was stirred at 0° for 10 minutes. TLC check in BPA indicated that no starting material was left after this relatively short period of contact, and that the only product was triamcinolone 21-acetate (compound 47a). The reaction product was neutralized by pouring into 12% sodium carbonate solution (200 ml) the solids were filtered, washed with abundant water, collected and dried. The pure triamcinolone tetrol (compound 47b) was obtained by saponification in methanol suspension (ref. B. Loken. G. Rosenkranz, U.S. Pat. No. 2,860,149, CA 91959, Jan. 14, 1957). Reaction of the triamcinolone tetrol (which in itself is a well known anti-inflammatory compound) with acetone under acid catalysis according to known methods leads to the formation of the Triamcinolone Acetonide (11β,21-dihydroxy-16α,17αisopropylidenedioxy-9αfluoro-pregna-1,4-diene3,20-dione) which is extensively used as an anti-inflammatory steroid (compound 49b).

EXAMPLE 24

To a suspension of 10 g of 11β-trimethylsiloxy-16α,17α-dihydroxy-21-acetoxy-9α-flouropregna-1,4-diene-3,20-dione (compound 46, from Example 22) in 100 ml of acetone, was added a solution of 0.2 ml perchloric acid (70%) in 10 ml of acetone. The mixture was stirred for 16 hours at room temperature, 20 ml of a saturated sodium bicarbonate solution added, and the mixture was concentrated to about 15 ml under reduced pressure. Complete precipitation was obtained by addition of 200 ml water. The product was filtered off, washed well with water, collected and dried. There was obtained (compound 48) 11β-trimethylsiloxy-21 -acetoxy-16α,1-7α-isopropylidenedioxy-9α-fluoro-pregna-1,4-diene-3,20-dione, in close to quantitative yield (10.75 g). Recrystallization from acetone-hexane provided the analytical sample which was pure on TLC (BPB).

IR bands are at 1760, 1730, 1670, 1635, 1615, 1260, 1230, 1085, 845 cm⁻¹.

EXAMPLE 25

1g of 11β-trimethylsiloxy21-acetoxy-16α,17α-isopropylidenedioxy-9α-fluoro-pregna-1,4-diene-3,20-dione (from Example 24) was powdered finely and suspended in 10 ml 49% aqueous hydrofluoric acid by stirring at 0°. After 7 minutes contact period about 5% of the starting material in a model experiment remained (by TLC (BPA)). The reaction product, after exactly 7 minutes contact, was neutralized by pouring into 12% sodium carbonate solution (200 ml), the solids were filtered, washed with water, collected and dried. Triamcinolone Acetonide, 21-acetate was obtained (compound 49a). The pure product was obtained in about 80% yield by recrystallization from chloroform-ethyl acetate. (If desired, Triamcinolone Acetonide can be obtained by saponification of the 21-acetate group.)

EXAMPLE 26

To a solution of compound 51, namely 9α-fluoroprednisolone, 21-acetate (18 g) in pyridine (54 ml) was added trimethylchlorosilane (8 ml). The mixture was stirred at 25° for a period of 60 hours, diluted with 200 ml of methylisobutyl ketone and washed with 10% aqueous sulfuric acid (2 × 200 ml) and water (260 ml). After drying with sodium sulfate, the solution was concentrated to a small volume under reduced pressure, to give a colorless crystalline residue of the 11-trimethylsilyl ether (compound 52) in quantitative yield. TLC indicated a homogenous product (System BPB, silica gel plate 254 )

Salient IR bands: 3400, 1760, 1730, 1665, 1620, 1610, 1260, 1240, 1080, 845 cm$^{-1}$.

There was obtained 21.0 g of 17α-hydroxy-21-acetoxy-11β-trimethylsiloxy-9α-fluoropregn-1,4-diene-3,20-dione. m.p. about 203°-204°.

EXAMPLE 27

A mixture of the 17α-hydroxy-21-acetoxy-11β-trimethylsiloxy-9α-fluoro-pregn-1,4-diene-3,20-dione from Example 26 (20.6 g) dichloromethane (50 ml) and acetic acid (20 ml) was treated with trifluoro-acetic anhydride (20 ml) for a period of 5 hours at 25°. The reaction mixture was diluted with methyl-isobutylketone (200 ml) and extracted with sodium bicarbonate solution (500 ml) and then with water (200 ml). The organic layer was dried over sodium sulfate, and evaporated to dryness under reduced pressure. The residue was amorphous, homogenous in TLC (BPB, silica plates No. 254). Crystalline 17α,21-diacetoxy-11β-trimethylsiloxy-9α-fluoropregna-1,4-diene-3,20 -dione (compound 53) was obtained directly from the residue by trituration with methanol.

Salient IR bands: 1760, 1740, 1670, 1635, 1610, 1260, 1240 1080, 840 cm$^{-1}$.

Crude yield (residue): 22.2 g; crystalline (triturated with methanol): 19.8 g with m.p. 162°-163°).

EXAMPLE 28

A mixture of 17α,21-diacetoxy-11β-trimethylsiloxy-9α-fluoropregna-1,4-diene-3,20-dione (4 g, from Example 27), anhydrous potassium acetate (4 g) and dimethylformamide (20 ml) was heated at 115° for 1.5 hours. The reaction mixture was cooled and poured into cold water, and dried under vacuum. A sample was crystallized from methanol. Homogenous on TLC (benzene-ether, 1:1).

Salient IR bands: 1710, 1670, 1640, 1615, 1590, 1225, 1070, 845 cm$^{-1}$.

Yield: 90-95%.

This product, which is 11β-trimethylsiloxy-21-acetoxy-9α-fluoro-pregna-1,4,16-triene-3,20-dione m.p. 212°-214° (compound 45) was treated according to Example 22 and the product subsequently converted to triamcinolone according to the method described in Example 23, and also to the triamcinolone acetonide as described in Example 25.

EXAMPLE 29

7.0 g of prednisolone 21-monoacetate was treated exactly as in Example 5 with trimethylchlorosilane in pyridine solution, there was obtained 8.0 g of 11β-trimethylsiloxy-17α-hydroxy-21-acetoxy-pregna-1,4-diene-3,20-dione. m.p. 180°-184° and 203°-204°, two allotropic forms.

IR: 3300, 1755, 1735, 1665, 1620, 1605, 1270, 1240, 1060, 845 cm$^{-1}$.

EXAMPLE 30

A mixture of 8 g of 11β-trimethylsiloxy-17α-hydroxy-21-acetoxy-pregna-1,4-diene-3,20-dione (from Example 29), 8 g of paratoluenesulfonic acid monohydrate and 800 ml of isopropenyl acetate was allowed to stand for one week at room temperature. By this time TLC control indicated that almost all the starting material had reacted. 15 g of anhydrous sodium acetate was added and the mixture left stirring for another day. The supernatant was decanted from the salt crystals and the resulting solution — after addition of 400 ml methylisobutyl ketone — was washed twice, each time with 500 ml of water, then with 200 ml of saturated aqueous sodium chloride solution, dried over anhydrous sodium sulfate, and evaporated under reduced pressure to dryness. This residue was found to be 11β-trimethylsiloxy-17α,21-diacetoxypregna-1,4-diene-3,20-dione, about 90% pure, there was about 10% of a less polar artifact believed to be the result of a slight aromatization side reaction about ring A, followed by acetylation. The identity was proved by hydrolyzing off the silyl ether blocking group to give prednisolone 17,21-diacetate, identified by TLC with a sample obtained by the Ortho ester route.

EXAMPLE 31

4 g of 11β-trimethylsiloxy-17α,21-diacetoxypregna-1,4-diene-3,20-dione (from Example 30) was treated with potassium acetate and dimethylformamide exactly as described in Example 28. There was obtained 11β-trimethylsiloxy-21-acetoxypregna-1,4,16-triene-3,20-dione (compound 55).

The conversion sequence described in Examples 29, 30, 31 of prednisolone 21-monoacetate to compound 55 has not been illustrated on the drawing since it parallels the conversion of 51→52→ 53→45, absent only presence of the 9αF substituent. The examples which follow describe a conversion sequence for compound 55 which parallels the conversions of compounds 45→49 again absent only the 9αF substituent.

EXAMPLE 32

A solution of 11β-trimethylsiloxy-17α,21-diacetoxy-pregna-1,4,16-triene-3,20-dione (1 g of compound 55 from Example 31) in acetone (50 ml) and formic acid was treated with a solution of potassium permanganate and worked up exactly as described in Example 24.There was obtained 11β-trimethylsiloxy-16α,17α-dihydroxy21-acetoxy-pregna-1,4-diene-3,20-dione.

TLC was homogenous, developed in BPA. Yield: 0.95 g..

EXAMPLE 33

0.95 g of 11β-trimethylsiloxy-16α,17α-dihydroxy-21-acetoxy pregna-1,4 -diene-3,20-dione from Example 32 was treated with 40% aqueous hydrofluoric acid exactly as described in Example 32, only this time with the 9α-fluoro substituent absent, the reaction was faster. The starting material had all reacted after 5 minutes of contact. No hydrolysis took place at the 21-acetate group, nor was there any aromatization side reaction about ring A, or any homo D annulation about ring D. There was obtained close to quantitative yield of 11β, 16α, 17α-trihydroxy-21-acetoxy-pregna-1,4-diene-3,20-dione which was converted to the acetonide according to the known methods. Acetone, perchloric acid as a catalyst. This acetonide (11β-hydroxy-21-acetoxy- 16α,17αisopropylidene-dioxypregna-1,4-diene-3,20-dione) was saponified in methanol suspension (ref. B. Löken, G. Rosenkranz, U.S. Pat. No. 2,860,143, CA 91959, January 14, 1957) to give Prednacinolone Acetonide which is a well known anti-inflammatory compound (see Am. Med. A. 213 1325 (1970)) i.e. 11β,21-dihydroxy-16α,17α-isopropylidendioxy-pregna-1,4-.diene-3,20-dione.

What is claimed:

1. A process for producing corticoids characterized by at least one of the following substituents:
    a. 6αF
    b. 16α,17αhydroxy or isopropylidenedioxy
    c. 16αorβmethyl
    d. Δ1,4 from an 11β-OH precursor steroid, of the pregnane series which comprises:
        1. reacting the 11β-OH precursor steroid with trimethylchlorosilane forming thereby the corresponding 11β-trimethyl-siloxy steroid;
        2. carrying out a multi-step reaction sequence incorporating at least one of the (a), (b), (c), (d) substituents into the 11β trimethyl siloxy steroid; and thereafter
        3. hydrolyzing off the trimethyl siloxy group to create the 11β-OH group.

2. The process of claim 1 wherein the hydrolysis of step 3) is effected by reacting the steroid with 40–60% aqueous HF.

3. The process of claim 2 wherein the hydrolysis reaction is halted in the 95–100% completion range just short of completion.

4. A process for incorporating a 6αF substituent in a 3-keto-4-ene-11β-hydroxy steroid of the pregnane series which comprises:
    a. reacting such steroid with trimethyl chlorosilane to form thereby the corresponding 11βtrimethyl siloxane steroid;
    b. reacting this siloxy steroid with isopropenyl acetate to form thereby a 3-acetoxy-pregna-3,5-diene-11β-trimethyl-siloxy steroid;
    c. reacting this diene with perchloryl fluoride forming the 3-keto-4-ene-6ξ-fluoro steroid; and then
    d. simultaneously acid hydrolyzing and isomerizing to form the 3-keto-4-ene-6α-fluoro-11β-hydroxy steroid.

5. A steroid conversion process which comprises reacting a steroid characterized by the following formula:

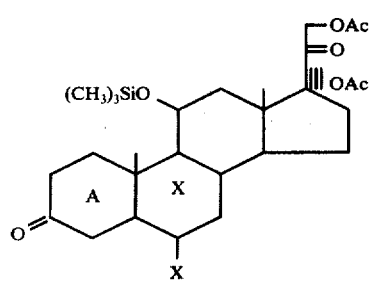

where: either X is αF and the other H, or both are H. The A ring is saturated, or 4-ene, or 1,4 diene with potassium acetate to convert the 17α-acetoxy steroid to the 16-ene steroid; thereafter reacting the 16-ene steroid with permanganate thereby hydroxylating the 16-ene steroid to the 16αOH, 17αOH steroid, and subsequently hydrolyzing away the silyl group.

6. The process of claim 5 wherein ring A. is saturated and the 16-ene siloxy steroid is subjected to DDQ dehydrogenation thereby producing a 1,4,16-triene steroid which thereafter is subjected to said permanganate hydroxylation reaction.

7. A steroid conversion process which comprises reacting a steroid characterized by the following formula:

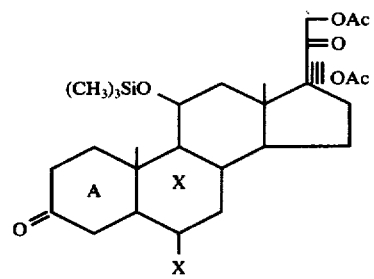

where: either X is αF and the other H, or both are H. The A ring is saturated, or 4-ene, or 1,4 diene with potassium acetate, thereby converting the 17α-acetoxy steroid to the 16-ene steroid; thereafter reacting the 16-ene steroid with lithium dimethyl copper thereby producing the 16αmethyl steroid and thereafter hydrolyzing away the silyl group.

8. A steroid conversion process which comprises reacting steroids characterized by the following structure:

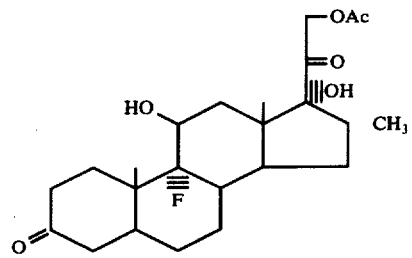

wherein the 16 methyl may be αmethyl or βmethyl with trimethyl chlorosilane to form thereby the 11βtrimethyl siloxane, then reacting the siloxane with DDQ to form thereby the $\Delta^{1,4}$ diene, and thereafter hydrolyzing the silyl ether group.

9. The process of claim 8 wherein the hydrolysis is effected by reacting the steroid with 40–60% aqueous HF.

10. The process of claim 1 wherein the multi-step reaction sequence of step 2 includes dichloro dicyanobenzoquinone dehydrogenation of the steroid to create a $\Delta^{1,4}$ substituent.

11. The process of claim 1 wherein the reaction sequence of step 2 includes a potassium acetate elimination of a 17α-acetoxy substituent to create thereby a 16-ene intermediate.

12. A steroid according to the following formula:

-continued

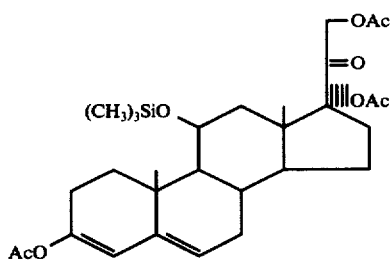

13. A steroid according to the following formula:

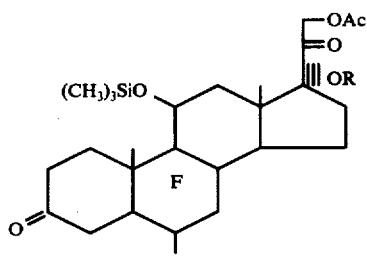

wherein R. is H or Ac.

14. A steroid according to the following formula:

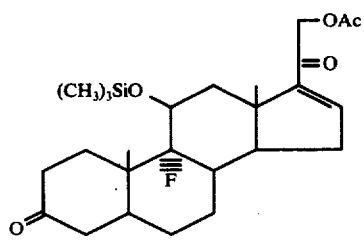

15. A steroid according to the following formula:

-continued

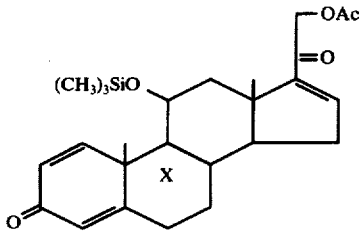

wherein X is H or αF.

16. A steroid according to the following formula:

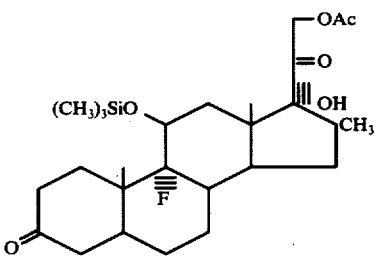

where 16 $CH_3$ may be 16α$CH_3$ or 16β$CH_3$.

17. A steroid according to the following formula:

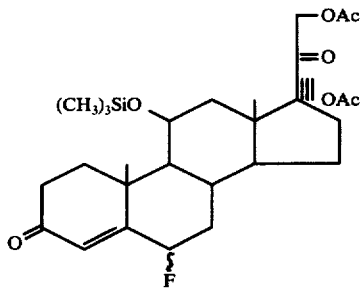

wherein the 6F may be alpha or epimeric.

18. A steroid according to the following formula:

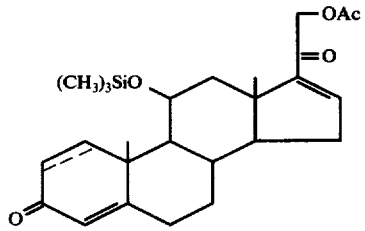

wherein the 1,2 linkage may be a single or a double bond.

* * * * *